United States Patent
Koka

(10) Patent No.: US 9,539,424 B2
(45) Date of Patent: Jan. 10, 2017

(54) SYSTEMS AND METHODS FOR ELICITING A STAPEDIAL REFLEX TO PROTECT HEARING

(71) Applicant: ADVANCED BIONICS AG, Staefa (CH)

(72) Inventor: Kanthaiah Koka, Superior, CO (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/779,269

(22) PCT Filed: Mar. 29, 2013

(86) PCT No.: PCT/US2013/034650
§ 371 (c)(1),
(2) Date: Sep. 22, 2015

(87) PCT Pub. No.: WO2014/158191
PCT Pub. Date: Oct. 2, 2014

(65) Prior Publication Data
US 2016/0051819 A1 Feb. 25, 2016

(51) Int. Cl.
*A61N 1/36* (2006.01)
*A61N 1/05* (2006.01)

(52) U.S. Cl.
CPC ......... *A61N 1/36032* (2013.01); *A61N 1/0541* (2013.01)

(58) Field of Classification Search
CPC .... A61N 1/36032; A61N 1/0541; A61N 1/08; A61N 1/05; A61B 5/6846; A61B 5/0031; A61B 5/076; A61B 5/6817; H04R 25/505; H04R 25/70; H04R 25/30
See application file for complete search history.

(56) References Cited

U.S. PATENT DOCUMENTS

| | | | |
|---|---|---|---|
| 3,271,520 A | 12/1962 | Fletcher et al. | |
| 4,958,372 A | 9/1990 | Carter | |
| 6,237,947 B1 | 5/2001 | Kausch | |
| 6,496,734 B1 | 12/2002 | Money | |

(Continued)

FOREIGN PATENT DOCUMENTS

| | | |
|---|---|---|
| WO | WO-2006/106480 | 10/2006 |
| WO | WO-2009/011939 | 1/2009 |

OTHER PUBLICATIONS

International Search Report and Written Opinion received in International Application No. PCT/US13/034650, dated Jun. 11, 2013.

*Primary Examiner* — Deborah Malamud
(74) *Attorney, Agent, or Firm* — ALG Intellectual Property, LLC

(57) ABSTRACT

An exemplary system includes 1) a sound detector configured to detect an audio signal, 2) an implantable stimulator configured to be implanted within a user, and 3) a sound processor communicatively coupled to the implantable cochlear stimulator and the sound detector. The sound processor is configured to determine that a level of the audio signal exceeds a predetermined threshold and direct, in response to the determination that the level of the audio signal exceeds the predetermined threshold, the implantable stimulator to elicit a stapedial reflex within the user by applying electrical stimulation to one or more stimulation sites within the user. Corresponding systems and methods are also disclosed.

20 Claims, 11 Drawing Sheets

(56) References Cited

U.S. PATENT DOCUMENTS

| | | | |
|---|---|---|---|
| 7,117,038 B1 | 10/2006 | Overstreet | |
| 7,804,964 B2 | 9/2010 | Schreiber | |
| 7,983,425 B2 | 7/2011 | Luo | |
| 8,103,354 B2 * | 1/2012 | Quick | A61B 5/121 |
| | | | 607/55 |

* cited by examiner

SYSTEMS AND METHODS FOR ELICITING A STAPEDIAL REFLEX TO PROTECT HEARING

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

In many people with sensorineural hearing loss, the hair cells deep within the cochlea that sense low frequencies are substantially undamaged. Such people may be able to hear low frequencies without assistance or by means of an amplifying hearing aid. However, due to impaired hearing, the remaining low frequency hearing may be vulnerable to accelerated deterioration. In particular, loss of hearing may increase the stapedial reflex threshold ("SRT") of a person. The SRT is the loudness at which the brain will cause the stapedial muscle to contract thereby applying tension to the ossicles of the inner ear and reducing the amplitude of vibrations reaching the cochlea by up to 25 dB. As the SRT rises, the low frequency hair cells of the cochlea are exposed to higher intensity vibrations for longer periods of time, thereby accelerating hearing loss and exposing the person to potentially damaging effects caused by sounds with relatively high intensity levels.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
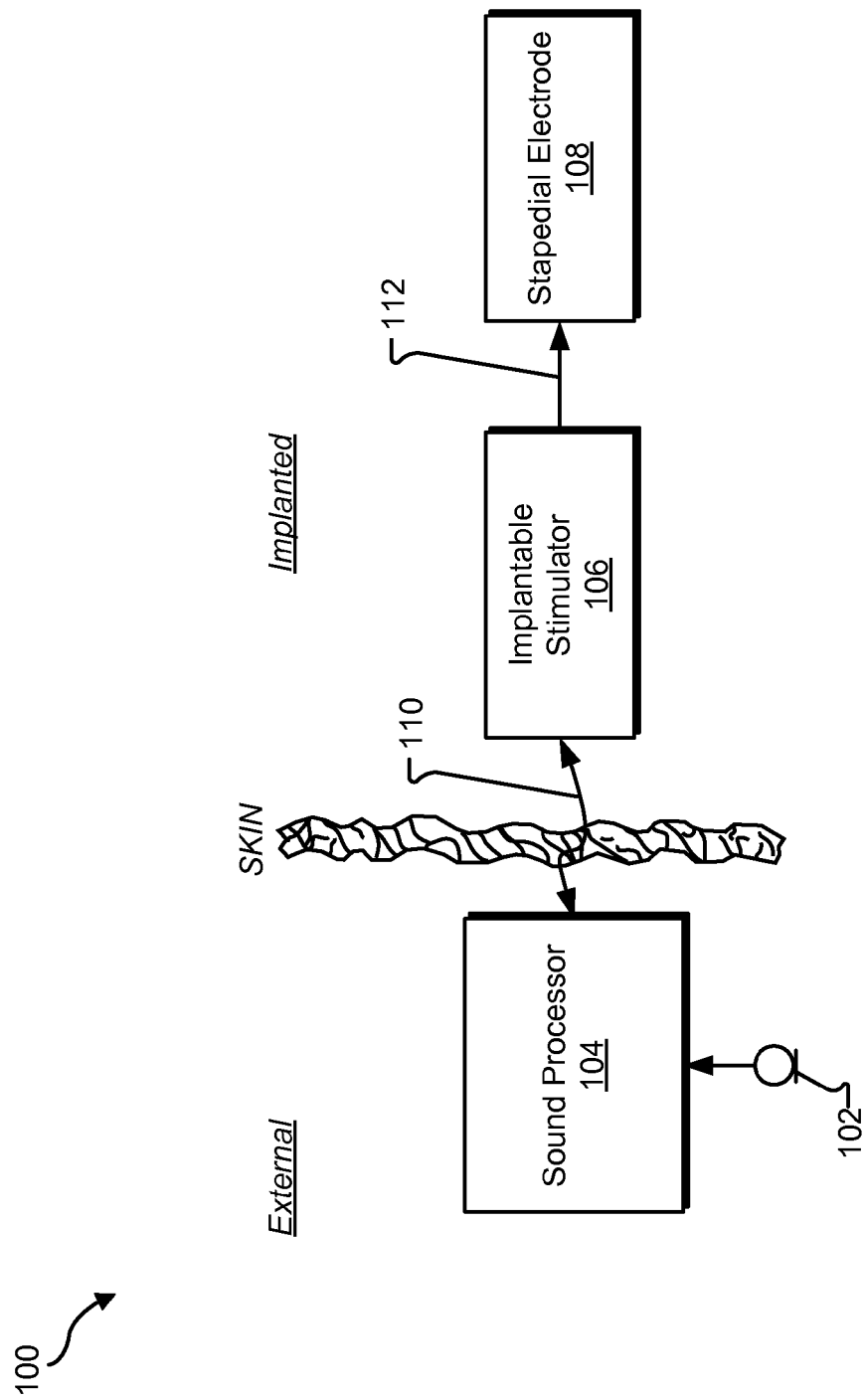
FIG. 1 illustrates an exemplary implantable hearing protection system according to principles described herein.

Systems and methods for eliciting a stapedial reflex of a user in order to protect hearing are described herein. An exemplary system includes a sound detector configured to detect an audio signal, an implantable stimulator configured to be implanted within a user, and a sound processor communicatively coupled to the implantable stimulator and the sound detector. The sound processor is configured to determine that a level of the audio signal exceeds a predetermined threshold, and, in response, direct the implantable stimulator to elicit a stapedial reflex within the user by applying electrical stimulation to one or more stimulation sites within the user.

In one exemplary implementation, the system includes a stapedial electrode communicatively coupled to the implantable stimulator and configured to be coupled to at least one of a stapedius tendon and a stapedius muscle of the user. In this implementation, the sound processor may be further configured to direct the implantable stimulator to elicit the stapedial reflex by applying the electrical stimulation to at least one of the stapedius tendon and the stapedius muscle by way of the stapedial electrode.

In another exemplary implementation, the system includes an intracochlear electrode array communicatively coupled to the implantable stimulator and configured to be implanted within a cochlea of the user. In this implementation, the sound processor may be further configured to direct the implantable stimulator to elicit the stapedial reflex by applying the electrical stimulation to one or more locations within the cochlea by way of the intracochlear electrode array. In some examples, only high-frequency electrodes (i.e., electrodes corresponding to a relatively high frequency band, such as frequencies greater than 1000 Hz) of the intracochlear electrode array are stimulated to elicit the stapedial reflex.

By electrically eliciting a stapedial reflex in response to detecting audio signals that have a level (e.g., a sound pressure level ("SPL"), a volume level, an intensity level, etc.) that exceeds a predetermined threshold, the systems and methods herein may help protect (e.g., preserve) a user's hearing (e.g., any hearing ability that the user may have, such as low frequency residual hearing that an electro-acoustic stimulation ("EAS") user may have). For example, by detecting that an incoming audio signal (e.g., an explosion, blast, or other noise) is relatively loud, the systems and methods herein may elicit a stapedial reflex in a manner that is "on-demand" (i.e., prior to the audio signal being processed by ears and/or brain of the user) and thereby force the stapedius muscle to be in a contracted state while the incoming audio signal is processed by the user. This may preserve hearing (e.g., residual hearing) in the user and/or otherwise protect the user from one or more damaging effects of the audio signals. Other benefits and/or advantages provided by the disclosed systems and methods will be made apparent herein.

FIG. 1 illustrates an exemplary hearing protection system 100 that may be configured to protect hearing in a user (i.e., a user of hearing protection system 100). Hearing protection system 100 may include a sound detector 102, a sound processor 104, an implantable stimulator 106, and a stapedial electrode 108. Additional or alternative components may be included within hearing protection system 100 as may serve a particular implementation.

As shown, hearing protection system 100 may include various components configured to be located external to a user including, but not limited to, a sound detector 102 and sound processor 104. Hearing protection system 100 may further include various components configured to be implanted within the user including, but not limited to, the implantable stimulator 106 coupled to the stapedial electrode 108. The stapedial electrode 108 may be coupled to a stapedius tendon, stapedius muscle, and/or an area of a user's inner ear proximate either of these members such that electrical stimulation can be applied to the stapedius muscle. As will be described in more detail below, additional or alternative components may be included within hearing protection system 100 as may serve a particular implementation. The components shown in FIG. 1 will now be described in more detail.

Sound detector 102 may be configured to detect audio signals presented to the user. Sound detector 102 may be implemented in any suitable manner. For example, sound detector 102 may include a microphone (e.g., a "T-Mic" or the like) that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104. Additionally or alternatively, sound detector 102 may be implemented by one or more microphones disposed within sound processor 104 and/or any other suitable microphone as may serve a particular implementation.

As will be described in greater detail below, the exemplary implementations disclosed herein are particularly useful for eliciting the stapedial reflex of users in response to loud noises. Accordingly, the sound detector 102 in the embodiment of FIG. 1 may, in some embodiments, include no more functionality than required to detect very loud sounds (e.g., sounds having a loudness level near a stapedial reflex threshold ("SRT") or some other arbitrary loudness threshold). Accordingly, sound detector 102 may include a microphone capable of detecting sound and outputting a signal representing that sound or as a device that produces an output in response to a loud sound that is not necessarily a faithful reproduction of the amplitude and/or frequency content of the loud sound. For example, a sound detector 102 may be embodied as an accelerometer, piezoelectric transducer, strain gauge, load cell, or any other device capable of detecting displacement or vibration due to a loud noise but not necessarily capable of accurately representing received sound in an output thereof sufficient to use the output to provide hearing assistance to the user.

In some exemplary implementations, the hearing protection system 100 of FIG. 1 may be used by those without hearing loss in order to preserve hearing. For example, people who work around loud noises may use the illustrated hearing protection system 100 to prevent hearing loss that may be caused by the loud noises. In particular, members of the military who work in bomb disposal or are otherwise proximate explosions and/or gunfire may be reluctant to wear hearing protection in a hostile environment due to the loss of awareness to threats. Accordingly, such individuals or others may use the hearing protection system 100 of FIG. 1 in order to provide hearing protection when needed.

Sound processor 104 (i.e., one or more components included within sound processor 104) may be configured to direct implantable stimulator 106 to generate and apply electrical stimulation (also referred to herein as "stimulation current") in response to one or more audio signals (e.g., one or more audio signals detected by sound detector 102, input by way of an input port, etc.) to one or more of a stapedius muscle, stapedius tendon, or adjacent area by means of the stapedial electrode 108. Sound processor 104 shown in FIG. 1 may include or be implemented by a behind-the-ear ("BTE") unit, a relatively small monitor, a body worn device, and/or any other sound processing unit as may serve a particular implementation.

In the exemplary implementation of FIG. 1, sound processor 104 may be configured to perform threshold detection with respect to an output of the sound detector 102. For example, sound processor 104 may be configured to determine whether a level (e.g., an SPL, a volume level, an intensity level, a power level, etc.) of an audio signal detected by sound detector 102 exceeds a predetermined threshold (e.g., a threshold SPL, a threshold volume level, a threshold intensity level, a threshold power level, etc.). This may be performed in any suitable manner.

For example, sound processor 104 may determine that the level of the audio signal exceeds the predetermined threshold by evaluating one or more of a voltage, current, and power level of an electrical output of sound detector 102 and determining that any of these levels are above a corresponding voltage threshold level, a corresponding current level, or a corresponding power level. In some examples, the threshold comparison may be performed by analog circuitry capable of performing threshold detection. Additionally or alternatively, the threshold comparison may be performed digitally by a programmable processor, digital signal processor ("DSP"), or other digital device.

As another example, sound processor 104 may determine that the level of the audio signal exceeds the predetermined threshold by detecting (e.g., predicting) that the level of the audio signal is going to exceed the predetermined threshold before the audio signal actually exceeds the predetermined threshold. For example, sound processor 104 may determine that a slope of an increase in the audio signal exceeds a predetermined slope. This may indicate that the audio signal is rapidly increasing in amplitude, for example, and that it will soon exceed the predetermined threshold. Other ways of determining that the level of the audio signal is going to exceed the predetermined threshold before the audio signal actually exceeds the predetermined threshold are described in U.S. Pat. No. 7,983,425, the contents of which are hereby incorporated by reference in their entirety.

By detecting that the level of the audio signal is going to exceed the predetermined threshold before the audio signal actually exceeds the predetermined threshold, sound processor 104 may have relatively more time to elicit a stapedial reflex that protect the user's hearing from any damaging effects that the audio signal may cause.

In response to a determination that the level of the audio signal exceeds the predetermined threshold, sound processor 104 may direct implantable stimulator 106 to elicit a stapedial reflex within the user by applying electrical stimulation to one or more stimulation sites within the user. For example, in the configuration of FIG. 1, sound processor 104 may direct implantable stimulator 106 to elicit the stapedial reflex by applying electrical stimulation to the stapedius muscle and/or stapedius tendon by way of stapedial electrode 108. This may be performed in any suitable manner. For example, sound processor 104 may generate an excitation signal and transmit this signal over a communication link 110 to the implantable stimulator 106, which then generates the electrical stimulation in accordance with the amplitude and/or frequency of the excitation signal. Alternatively, sound processor 104 may generate a drive signal (e.g., a signal that includes one or more stimulation parameters) that is transmitted to the implantable stimulator 106, which then responds to the drive signal by generating the stimulation current (e.g., in accordance with one or more stimulation parameters included in the drive signal).

The stimulation current applied by implantable stimulator 106 to stapedial electrode 108 may be configured to elicit the stapedial reflex of the user, i.e., cause contraction of the stapedius muscle. The stimulation current may be a direct current or alternating current signal and may have attributes such as amplitude, frequency, duty cycle, pulse width, and the like, effective to cause contraction of the stapedius muscle without damaging the stapedius muscle, stapedius tendon, or surrounding tissues.

In some examples, sound processor 104 may wirelessly transmit signals (e.g., excitation signals, drive signals, stimulation parameters (e.g., in the form of data words included in a forward telemetry sequence or analog signals), and/or power signals) to implantable stimulator 106 by way of wireless communication link 110. It will be understood that communication link 110 may include a bi-directional communication link and/or one or more dedicated unidirectional communication links. For example, communication link 110 may be implemented by sound processor 104 and implantable stimulator 106 by means of inductive coils, capacitive plates, radio frequency antennas, and/or any other structure for generating or receiving an electromagnetic field and corresponding circuits for interfacing with any of these structures.

Implantable stimulator 106 shown in FIG. 1 may include any type of implantable stimulator that may be used in association with the systems and methods described herein. For example, implantable stimulator 106 may include a relatively small intra-ear canal device (e.g., an actuator) configured to provide electrical stimulation by way of one or more electrodes coupled thereto. Such a device may be beneficial to users who would like to avail themselves of the features described herein while minimizing the surgical invasiveness that may occur with respect to larger types of implantable stimulators. Alternatively, as will be described below, implantable stimulator 106 may be implemented by a cochlear implant or the like that is configured to generate stimulation current representative of an audio signal processed by sound processor 104 (e.g., an audio signal detected by sound detector 102) in accordance with one or more stimulation parameters transmitted thereto by sound processor 104. Implantable stimulator 106 may be further coupled to the stapedial electrode 108, such as by means of a lead 112.

Figure 2:
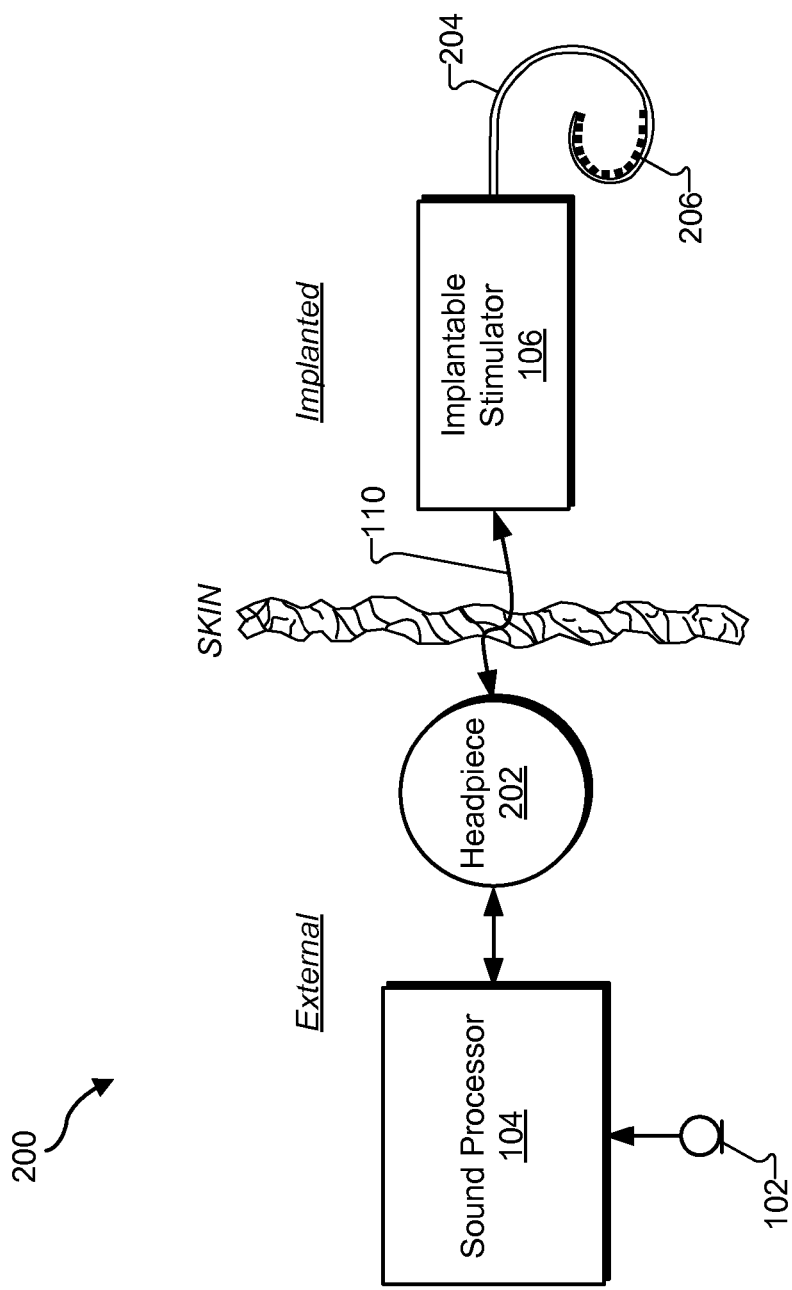
FIG. 2 illustrates another exemplary implantable hearing protection system according to principles described herein.

FIG. 2 illustrates another exemplary hearing protection system 200 that may be configured to protect hearing in a user (i.e., a user of hearing protection system 200). Hearing protection system 200 is similar to hearing protection system 100 in that it includes sound detector 102, sound processor 104, and implantable stimulator 106. However, as shown, hearing protection system 200 may additionally include a headpiece 202 and a lead 204 with a plurality of electrodes 206 disposed thereon, the plurality of electrodes defining an intracochlear electrode array. Hence, hearing protection system 200 may also be referred to as a cochlear implant system. Additional or alternative components may be included within hearing protection system 100 as may serve a particular implementation.

In the exemplary implementation of FIG. 2, sound processor 104 (i.e., one or more components included within sound processor 104) may be configured to direct implantable stimulator 106 to generate and apply electrical stimulation representative of one or more audio signals (e.g., one or more audio signals detected by sound detector 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling implantable stimulator 106. Sound processor 104 shown in FIG. 2 may include or be implemented by a behind-the-ear ("BTE") unit, a body worn device, and/or any other sound processing unit as may serve a particular implementation.

Headpiece 202 may be communicatively coupled to sound processor 104 and may include an external antenna (e.g., a coil and/or one or more wireless communication components) configured to facilitate selective wireless coupling of sound processor 104 to implantable stimulator 106. Headpiece 202 may be additionally or alternatively be used to selectively and wirelessly couple any other external device to implantable stimulator 106. To this end, headpiece 202 may be configured to be affixed to the user's head and positioned such that the external antenna housed within headpiece 202 is communicatively coupled to a corresponding implantable antenna (which may also be implemented by a coil and/or one or more wireless communication components) included within or otherwise associated with implantable stimulator 106. In this manner, stimulation parameters and/or power signals may be wirelessly transmitted between sound processor 104 and implantable stimulator 106 via the communication link 110.

Implantable stimulator 106 shown in FIG. 2 may include any type of implantable stimulator that may be used in association with the systems and methods described herein. For example, implantable stimulator 106 may be implemented by an implantable cochlear stimulator. In some alternative implementations, implantable stimulator 106 may include a brainstem implant and/or any other type of cochlear implant that may be implanted within a user and configured to apply stimulation to one or more stimulation sites located along an auditory pathway of a user.

In some examples, implantable stimulator 106 may be configured to generate electrical stimulation representative of an audio signal processed by sound processor 104 (e.g., an audio signal detected by sound detector 102) in accordance with one or more stimulation parameters transmitted thereto by sound processor 104. Implantable stimulator 106 may be further configured to apply the electrical stimulation to one or more stimulation sites within the user via one or more electrodes 206 disposed along lead 204. In some examples, implantable stimulator 106 may include a plurality of independent current sources each associated with a channel defined by one or more of electrodes 206. In this manner, different stimulation current levels may be applied to multiple stimulation sites simultaneously by way of multiple electrodes 206.

In some examples, in response to a determination that a level of an audio signal exceeds a predetermined threshold, sound processor 104 may direct implantable stimulator 106 to elicit a stapedial reflex by applying electrical stimulation to one or more locations within the cochlea of the user by way of one or more electrodes 206 (i.e., by way of an intracochlear electrode array). To ensure that a stapedius reflex is elicited in response to the electrical stimulation, the electrical stimulation may have a current level substantially equal to a most comfortable current level ("M level") associated with the user.

Sound processor 104 may be further configured to protect the user from damaging effects of a high level audio signal by abstaining from directing implantable stimulator 106 to apply electrical stimulation representative of the audio signal by way of one or more electrodes 206 (e.g., by bypassing some or all of the sound processing functionality of sound processor 104, as will be described in more detail below). For example, as described above, in response determining that the level of an audio signal exceeds a predetermined threshold, sound processor 104 may direct implantable stimulator 106 to elicit a stapedial reflex by applying electrical stimulation to one or more locations within the cochlea of the user by way of one or more electrodes 206. However, sound processor 104 may abstain from directing implantable stimulator 106 to apply additional electrical stimulation that is representative of the audio signal by way of electrodes 206. In this manner, sound processor 104 may prevent damage that may be caused by applying electrical stimulation representative of the high level audio signal. Alternatively, sound processor 104 may attenuate the audio signal prior to directing implantable stimulator 106 to apply electrical stimulation representative of the audio signal to the user.

Figure 3:
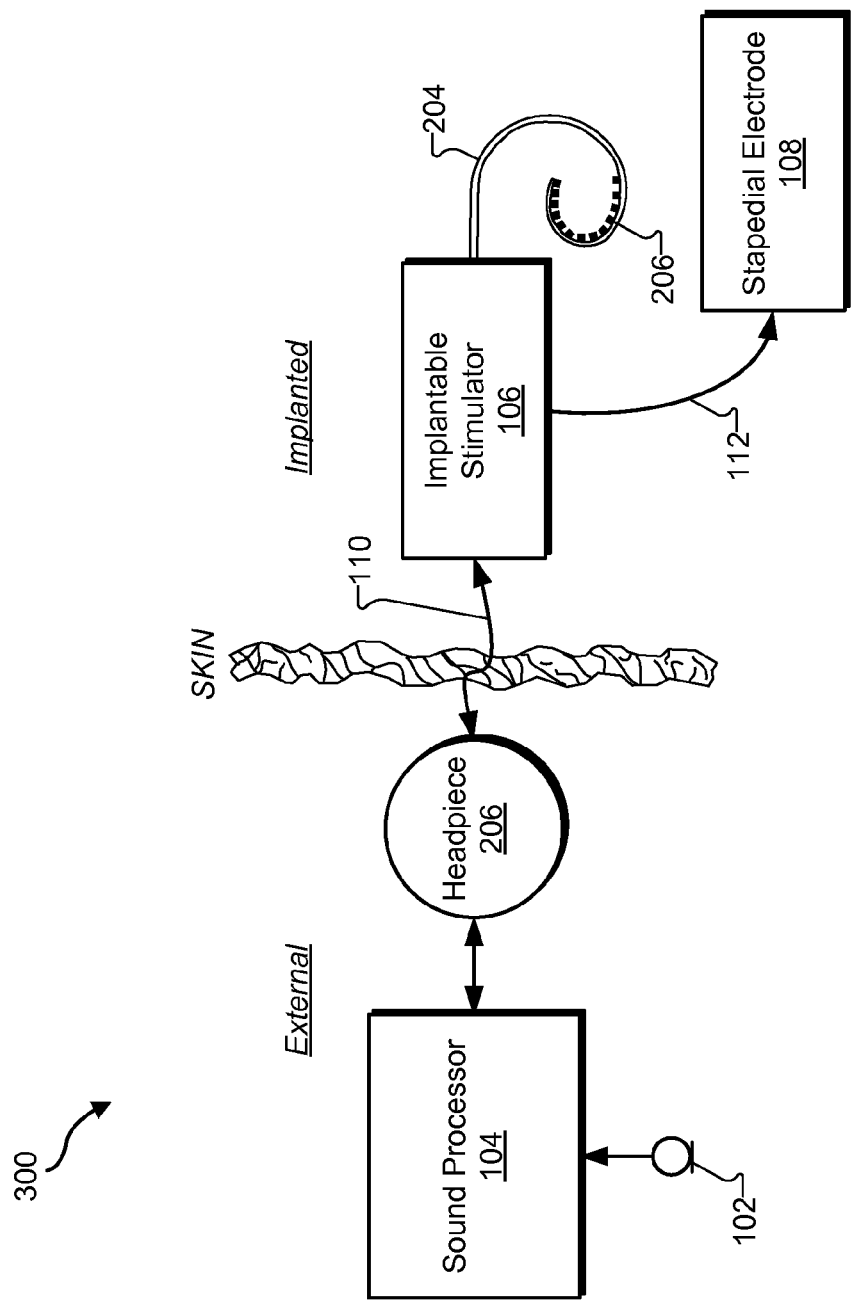
FIG. 3 illustrates another exemplary implantable hearing protection system according to principles described herein.

FIG. 3 illustrates another exemplary hearing protection system 300 that may be used in accordance with the systems and methods described herein. As shown, hearing protection system 300 includes both a stapedial electrode 108 and an intracochlear electrode array (i.e., electrodes 206). In this configuration, sound processor 104 may direct implantable stimulator 106 to elicit a stapedius reflex by applying electrical stimulation to the stapedius muscle and/or stapedius tendon by way of stapedial electrode 108 and/or by applying electrical stimulation to one or more stimulation sites within the cochlea by way of one or more electrodes 206.

Figure 4:
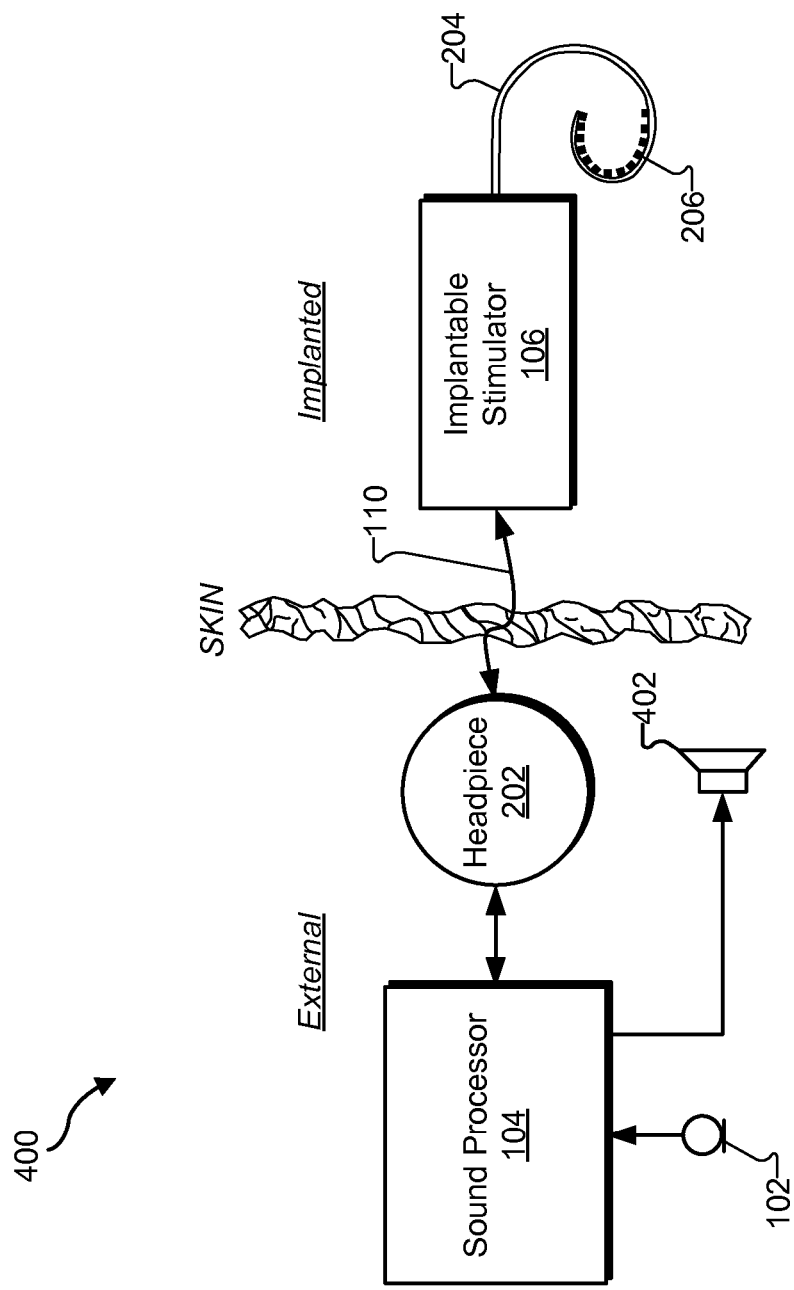
FIG. 4 illustrates another exemplary implantable hearing protection system according to principles described herein.

FIG. 4 illustrates another hearing protection system 400 that may be used in accordance with the systems and methods described herein. Hearing protection system 400 is similar to hearing protection system 200, except that hearing protection system 100 further includes a receiver 402 (which may be implemented as a loudspeaker or insert earphone) configured to provide acoustic stimulation to the user. Hence, hearing protection system 400 may be referred to as an electro-acoustic stimulation ("EAS") system.

Hearing protection system 400 may be used by users who have some degree of low frequency residual hearing (e.g., below 1000 Hz). For example, sound processor 104 may be configured to direct receiver 402 to apply acoustic stimulation representative of audio content included in a relatively low frequency band (e.g., below 1000 Hz) to the user and implantable stimulator 106 to apply electrical stimulation representative of audio content included in a relatively high frequency band (e.g., above 1000 Hz) to one or more stimulation sites within the user by way of one or more of electrodes 206.

In the configuration shown in FIG. 4, sound processor 104 may be configured to direct implantable stimulator 106 to elicit a stapedius reflex in response to a determination that a level of an audio signal exceeds a predetermined threshold in any of the ways described herein. For example, sound processor 104 may direct implantable stimulator 106 to elicit a stapedial reflex by applying electrical stimulation to one or more locations within the cochlea of the user by way of one or more electrodes 206. In some embodiments, hearing protection system 400 may further include stapedial electrode 108, which may also be used to electrically elicit the stapedius reflex.

In some examples, sound processor 104 may additionally or alternatively elicit a stapedial reflex to protect hearing by applying acoustic stimulation to the user by way of receiver 402. The acoustic stimulation may have any suitable characteristic as may serve a particular implementation. For example, the acoustic stimulation may include a relatively low frequency tone burst (e.g., a 125 Hz tone burst).

By electrically and/or acoustically eliciting a stapedius reflex in an EAS user in response to a determination that an incoming audio signal has a relatively high level, hearing protection system 400 may assist in preserving the EAS user's residual low frequency hearing.

Figure 5:
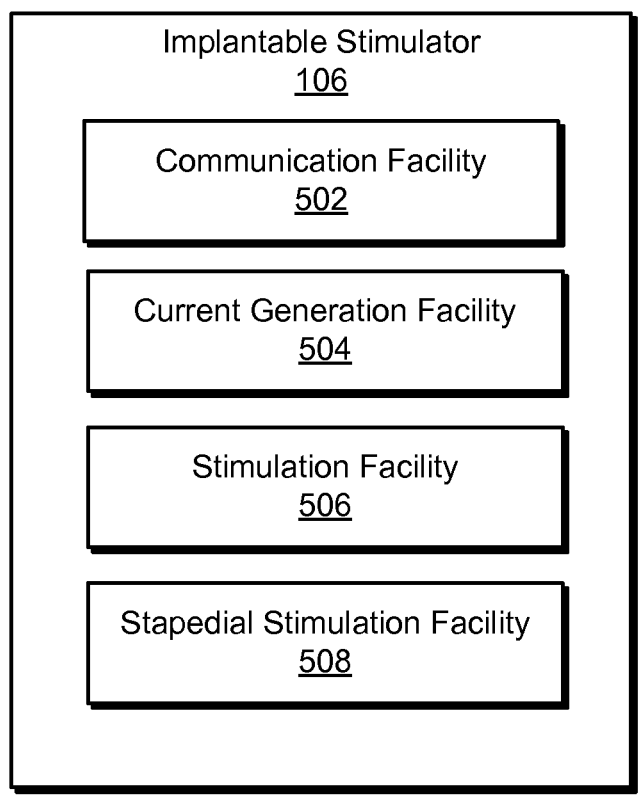
FIG. 5 illustrates exemplary components that may be included within an implantable stimulator according to principles described herein.

FIG. 5 illustrates exemplary components of implantable stimulator 106. As shown in FIG. 5, implantable stimulator 106 may include a communication facility 502, a current generation facility 504, a stimulation facility 506, and a stapedial stimulation facility 508, which may be in communication with one another using any suitable communication technologies. Each of these facilities 502-508 may include any combination of hardware, software, and/or firmware as may serve a particular application. For example, one or more of facilities 502-508 may include a computing device or processor configured to perform one or more of the functions described herein. Facilities 502-508 will now be described in more detail.

Communication facility 502 may be configured to facilitate communication between implantable stimulator 106 and sound processor 104. For example, communication facility 502 may include one or more coils configured to receive control signals and/or power via one or more communication links 110 to implantable stimulator 106.

Current generation facility 504 may be configured to generate stimulation current in accordance with one or more stimulation parameters received from sound processor 104. To this end, current generation facility 504 may include one or more current generators and/or any other circuitry configured to generate stimulation current. For example, current generation facility 504 may include an array of independent current generators each corresponding to a distinct electrode 206 or channel. For exemplary hearing protection systems that include stapedial electrode 108, current generation facility 504 may additionally or alternatively include a current generator configured to generate stimulation current for application to the stapedial electrode 108 responsive to control signals from the sound processor 104.

Stimulation facility 506 may be configured to facilitate application of the stimulation current generated by current generation facility 504 to one or more stimulation sites within the user in accordance with one or more stimulation parameters received from sound processor 104. To this end, stimulation facility 506 may be configured to interface with the one or more electrodes 206 by means of the lead 204. For hearing protection systems that include a stapedial electrode 108, stimulation facility 506 may additionally or alternatively be configured to facilitate application of the stimulation current generated by current generation facility 504 to the stapedial electrode 108.

The exemplary implementations described herein advantageously provide means to stimulate the stapedial reflex of a user in response to loud noises such that the user's hearing may be protected (e.g., by preserving an ability of the user to hear normally, preserving the user's residual hearing, etc.). In order to improve the degree of protection, the stimulation of the stapedius muscle may occur as soon as possible in order to reduce the amount of time that the cochlea of the user is exposed to vibrations without damping due to the stapedial reflex.

Accordingly, in some exemplary implementations, implantable stimulator 106 may include a stapedial stimulation facility 508 to more quickly stimulate the stapedial electrode 108. The stapedial stimulation facility 508 may define a separate path for control signals from the sound processor 104 directing stimulation of the stapedial electrode 108 to be translated into current applied to the stapedial electrode 108. In other examples, the stapedial stimulation facility 508 is omitted and stimulation current for the stapedial electrode 108 is generated in the same manner using the same facilities 502-508 as used to stimulate the electrodes 206. The stapedial stimulation facility 508 may include one or both of separate hardware paths and separate software paths in the data/signal flow by which a control signal received over the communication link 110 is translated into a current applied to the lead 112 of the stapedial electrode 108 by the implantable stimulator.

Figure 6:
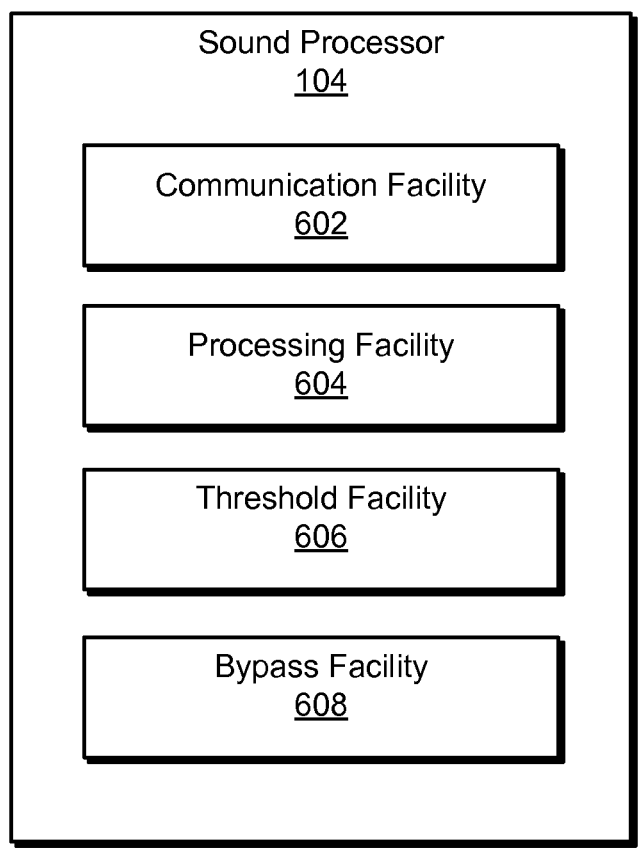
FIG. 6 illustrates exemplary components that may be included within a sound processor according to principles described herein.

FIG. 6 illustrates exemplary components of sound processor 104. As shown in FIG. 6, sound processor 104 may include a communication facility 602, a processing facility 604, a threshold facility 606, and a bypass facility 608, any or all of which may be in communication with one another using any suitable communication technologies. Each of these facilities 602-608 may include or be implemented by any combination of hardware, software, and/or firmware as may serve a particular application. For example, one or more of facilities 602-608 may include or be implemented by a computing device or processor configured to perform one or more of the functions described herein. It will also be recognized that one or more of facilities 602-608 may be optionally not included within sound processor 104. Facilities 602-608 will now be described in more detail.

Communication facility 602 may be configured to facilitate communication between sound processor 104 and implantable stimulator 106. For example, communication facility 602 may include transceiver components configured to wirelessly transmit data (e.g., control parameters and/or power signals) to implantable stimulator 106 by way of a coil included in headpiece 202.

Processing facility 604 may be configured to perform one or more signal processing heuristics on an audio signal presented to the user, such as an output of sound detector 102. For example, processing facility 604 may perform one or more pre-processing operations, spectral analysis operations, noise reduction operations, mapping operations, and/or any other types of signal processing operations on a detected audio signal as may serve a particular application. In some examples, processing facility 604 may generate one or more control parameters governing an operation of implantable stimulator 106 (e.g., one or more stimulation parameters defining the electrical stimulation to be generated and applied by implantable stimulator 106).

Threshold facility 606 may be configured to evaluate an output of the sound detector 102 with respect to a threshold. The threshold may correspond to an estimate of a level such that for sound below that level no significant loss of hearing will occur and sound above that level will cause loss of hearing. In some examples, the threshold facility 606 is configured to sample the output of the sound detector 102 periodically and compare the sample to the threshold. For example, the processing facility may sample an output of the sound detector 102 and convert the samples to binary values. Threshold facility 606 may then periodically sample these binary values.

In a healthy person, the time between the commencement of an above-SRT sound and the stapedial reflex is about 10 to 20 ms. However, in many instances, this response time is too slow to prevent substantial damage to a person's hearing. In particular, for a person with hearing loss, the loudness at which the stapedial reflex is elicited is higher than the loudness above which hearing damage occurs, even with use of a hearing protection system, such as any of the hearing protection systems described herein. Accordingly, the hearing protection systems described herein may advantageously elicit the stapedial reflex both faster and at a lower loudness threshold than the naturally occurring stapedial reflex of the user.

To that end, the sampling period for threshold facility 606 may be substantially smaller than 10 to 20 ms. In general, the sampling period may be as short as possible without perceptibly degrading the quality of hearing assistance provided by the hearing protection systems described herein due to interruption of the processing facility 604. For example, the sampling period may be between 5 µs and 1 ms (e.g., 10 µs). Stated differently, the threshold facility 606 may sample one of every N digital samples from the output of the sound detector 102, where N is chosen to be as small as possible without perceptibly degrading hearing assistance provided by the hearing protection system 100. For example, N may be between 100 and 500 samples.

As noted above, in order to reduce hearing loss, the stapedial reflex is advantageously elicited as soon as possible. Accordingly, bypass facility 608 may be configured to bypass some or all of the sound processing functionality of the processing facility 604 used to transmit a drive signal to implantable stimulator 106. Bypass facility 608 may be a software bypass or a hardware bypass. For example, in response to a determination that a level of an audio signal exceeds the predetermined threshold, bypass facility 608 may generate a drive signal instructing implantable stimulator 106 to stimulate one or more stimulation sites effective to elicit the stapedial reflex. The drive signal may not relate to the actual output of sound detector 102. For example, the drive signal may be a predefined signal or signal generated according to predefined parameters. Inasmuch as the drive signal is not based on the actual output of the sound detector 102, functions of the processing facility 604 may be bypassed, such as one or more pre-processing operations, spectral analysis operations, noise reduction operations, mapping operations, and/or any other types of signal processing operations on a detected audio signal as may serve a particular application.

In some example implementations, bypass facility 608 includes a separate hardware path from threshold facility 606 to headpiece 202. Accordingly, threshold facility 606 may utilize the separate hardware path to transmit a drive signal to headpiece 202 upon detecting exceeding of the threshold by the output of the sound detector 102.

Figure 7:
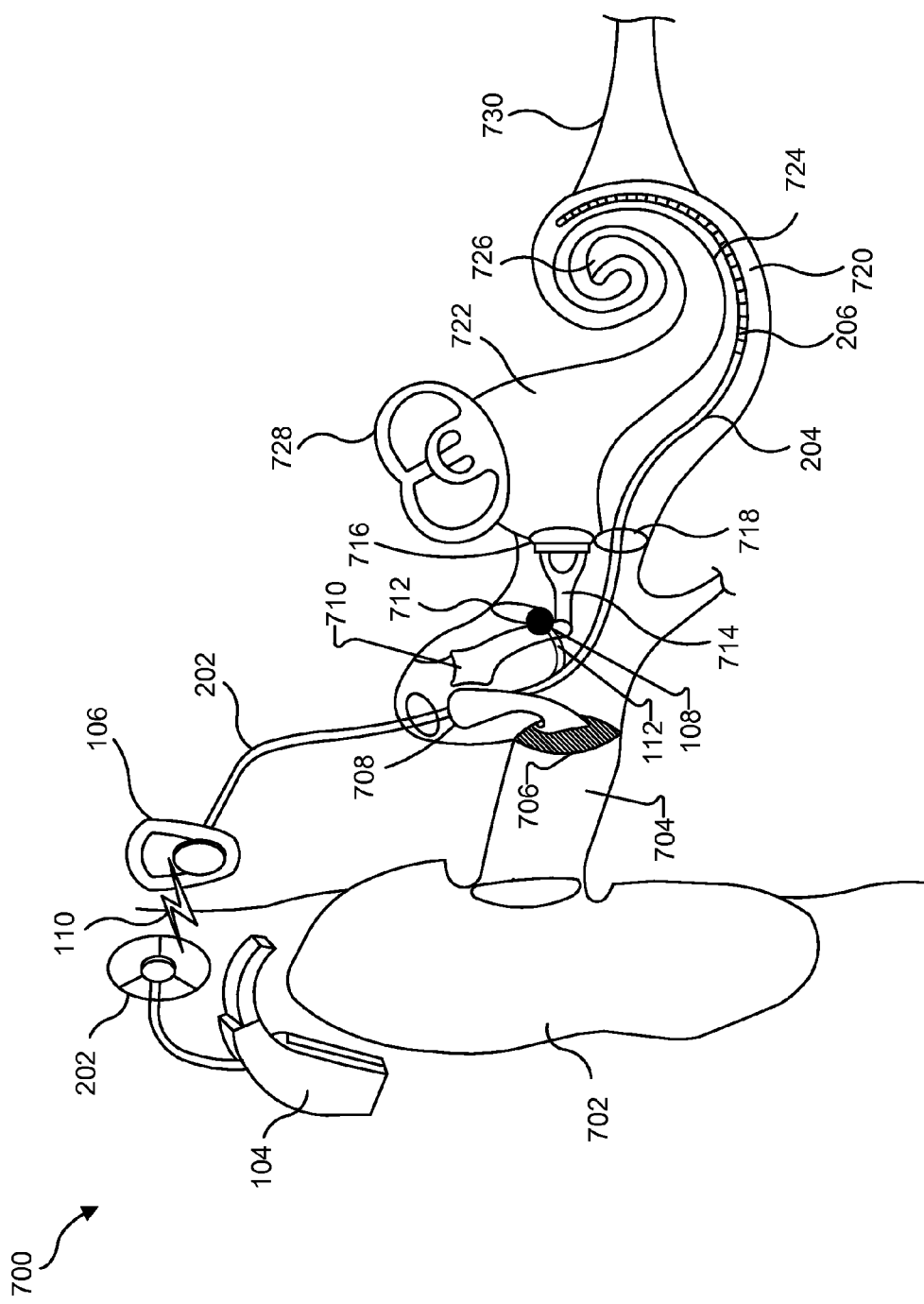
FIG. 7 illustrates an exemplary implementation of an implantable hearing protection system incorporating a stapedial electrode according to principles described herein.

FIG. 7 illustrates an exemplary implementation 700 of hearing protection system 300 wherein implantable stimulator 106, intracochlear electrodes 206, and stapedial electrode 108 are implanted within a user. FIG. 7 also shows various anatomical features associated with the perception of sound, some of which will now be described in order to facilitate an understanding of the systems and methods described herein.

As shown in FIG. 7, the ear may include a pinna 702, ear canal 704, tympanic membrane 706, malleus 708, incus 710, stapedius muscle 712, stapes 714, oval window 716, round window 718, various structures within the cochlea (e.g., the scala tympani 720, the scala vestibuli 722, the basilar membrane 724, and the helicotrema 726), the labyrinth 728, and the auditory nerve 730. In a normally functioning ear, the tympanic membrane 706 vibrates in response to ambient sound, and via the ossicular chain (which includes the malleus 708, the incus 710, and the stapes 714), the vibration is transferred to the oval window 716. The stapedius muscle 712 acts as a hearing damper by exerting a force on the stapes 714 and thereby increasing the impedance of the middle ear when uncomfortable sound levels are detected. The damping caused by contraction of the stapedius muscle 712 may be on the order of approximately 20 dB.

As shown in FIG. 7, sound processor 104 may be located external to the user and mounted behind the ear, i.e., pinna 702. Headpiece 202 is positioned such that a coil disposed therein may be inductively coupled to a corresponding coil included within implantable stimulator 106. In this manner, sound processor 104 may transmit control parameters to implantable stimulator 106 by way of communication link 110. Lead 204 may also be implanted within the user such that electrodes 206 are disposed within the cochlea. Implantable stimulator 106 may generate and apply electrical stimulation to one or more stimulation sites within the cochlea via electrodes 206. Lead 112 also extends from implantable stimulator 106 to stapedial electrode 108, which may be secured to, or in otherwise in contact with, the stapedius muscle, the stapedius tendon, and/or an area adjacent either of these members.

Figure 8:
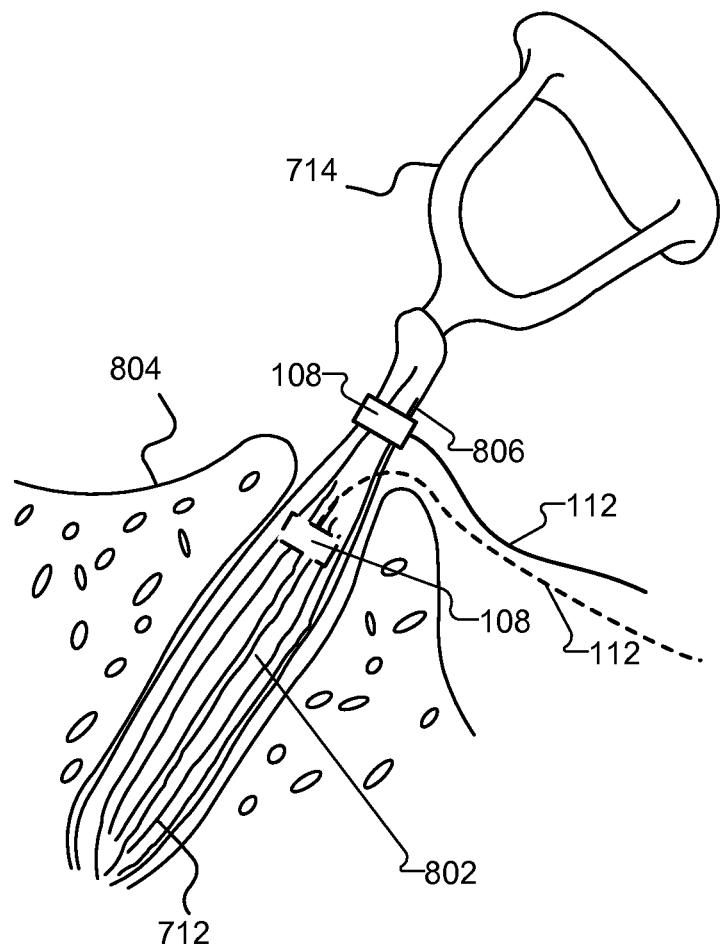
FIG. 8 shows the placement of a stapedial electrode with respect to the morphology of the stapedius muscle according to principles described herein.

FIG. 8 shows details of morphology of the stapedius muscle 712 and shows that a belly 802 of the stapedius muscle 712 is surrounded by a bone structure referred to as the pyramidal eminence 804. The belly 802 of the stapedius muscle 812 is connected to the stapes 714 by the stapedius tendon 806, a portion of which is not surrounded by the pyramidal eminence 804.

The stapedial electrode 108 may secure to or contact one or both of the stapedius tendon 806 and the belly 802 of the stapedius muscle 712. In some examples, the stapedial electrode 108 may be embodied as a band or clamp partially or completely encircling the stapedius tendon 806. In other examples, the stapedial electrode 108 is embedded within the belly 802 of the stapedius muscle. In still other examples, the stapedial electrode 108 secures to the tissue of the pyramidal eminence 804 at a location such that current from the stapedial electrode 108 is effective to stimulate the stapedius muscle 712.

Figure 9:
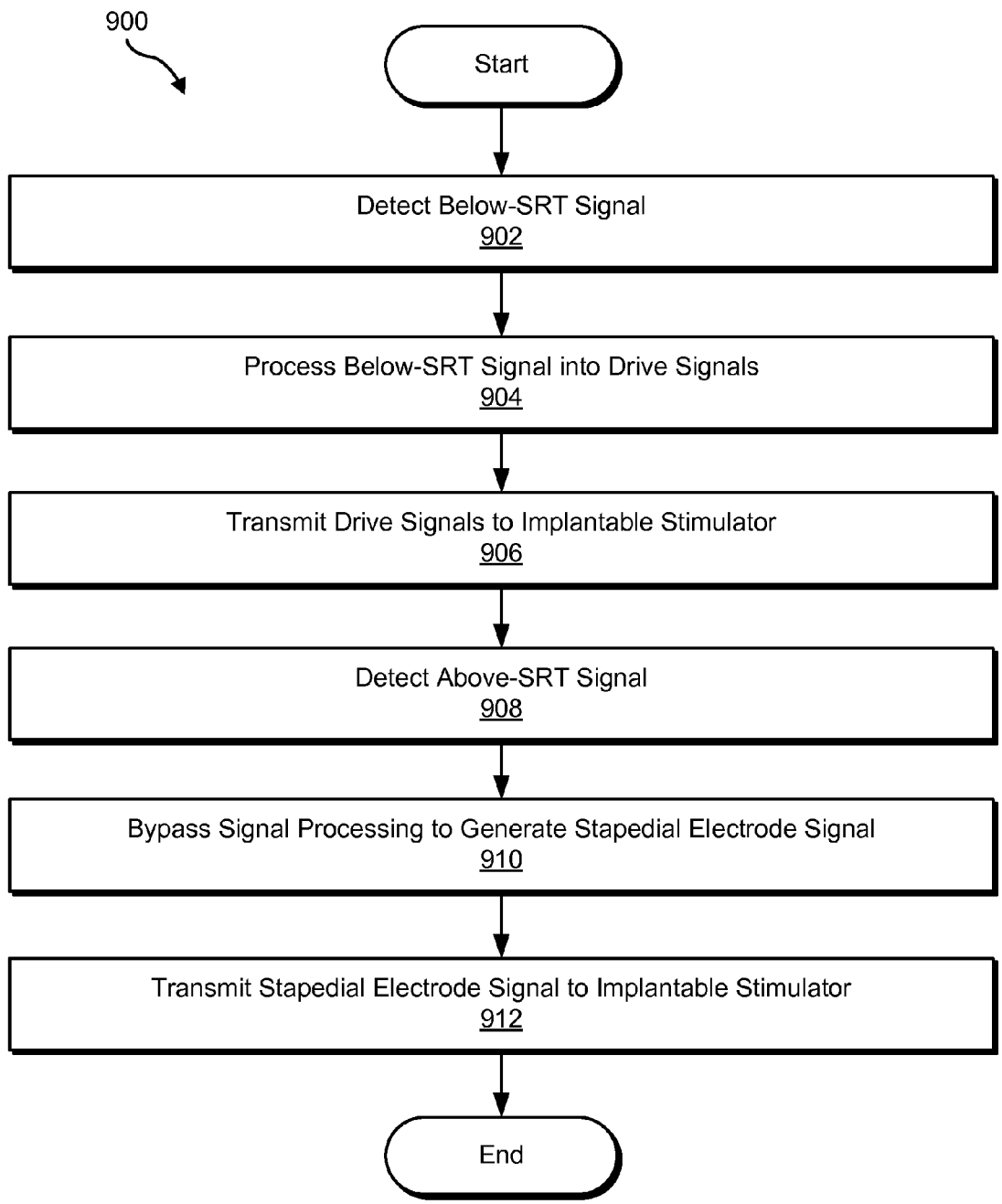
FIG. 9 illustrates an exemplary method of protecting hearing using a stapedial electrode according to principles described herein.

FIG. 9 illustrates an exemplary method 900 of eliciting the stapedial reflex of a user using a stapedial electrode. While FIG. 9 illustrates exemplary steps according to one exemplary implementation, other implementations may omit, add to, reorder, and/or modify any of the steps shown in FIG. 9. One or more of the steps shown in FIG. 9 may be performed by a sound processor 104 and/or any implementation thereof.

At step 902, the sound processor 104 detects a below-SRT signal. A below-SRT signal may be a signal for which the output of the sound detector 102 is below a predefined threshold that corresponds to a loudness at or below an estimated stapedial reflex threshold (SRT) of humans in general or specific to the user.

At step 904, the sound processor 104 processes the below-SRT signal into drive signals. As discussed above, the drive signals are configured to direct the implantable simulator 106 to apply stimulation currents to the electrodes 206 positioned in a cochlea of a user. The drive signals may be based on the amplitude and frequency content of the below-SRT signal such that the stimulation currents are effective to give the user perception of sound corresponding to the below-SRT signal.

At step 906, the sound processor 104 transmits the drive signals corresponding to the below-SRT signal to the implantable stimulator 106. As discussed, above, the implantable stimulator then generates stimulation current for the electrodes 206 positioned in the cochlea of the user according to the drive signals.

At step 908, the sound processor 104 detects an above-SRT signal. An above-SRT signal may be a signal for which the output of the sound detector 102 is above the predefined threshold of step 902 or some other threshold that generally corresponds to an estimated SRT of humans in general or the user.

At step 910, the sound processor 104 responds to the above-SRT signal by bypassing signal processing to generate a stapedial electrode signal. The stapedial electrode signal may direct the implantable electrode 106 to apply stimulation current to the stapedial electrode 108. Bypassing signal processing may include bypassing some or all of the steps required to generate drive signals representing the above-SRT signal, such as one or more pre-processing operations, spectral analysis operations, noise reduction operations, mapping operations, and/or any other types of signal processing operations on a detected audio signal as may serve a particular application. As noted above, bypassing may include executing a software bypass whereby code defining some or all of these signal processing function is not executed with respect to the above-SRT signal or is not executed until after the sound processor 104 has responded to the above-SRT signal. As also noted above, bypassing may include invoking a hardware bypass whereby logic encoding sound processing functionality is bypassed by a separate circuit for responding to above-SRT signals.

At step 912, the sound processor 104 transmits the stapedial electrode signal to the implantable electrode 106, which then generates corresponding stimulation current that is applied to the stapedial electrode 108. The stimulation current applied to the stapedial electrode may be effective to elicit contraction of the stapedius muscle effective to attenuate vibrations reaching the cochlea of the user (e.g., by at least 20 dB).

As noted above, other exemplary implementations of the method 900 may omit, add to, reorder, and/or modify any of the steps shown in FIG. 9. For example, where the sound processor 104 is incorporated into the exemplary implementation of hearing protection system 100 shown in FIG. 1, e.g. lacking intracochlear electrodes 206, steps 902-906 may be omitted. Likewise, at step 910, the sound processor 910 may generate a stapedial electrode signal without bypassing sound processing logic inasmuch as it may not be present in the sound processor 104.

Figure 10:
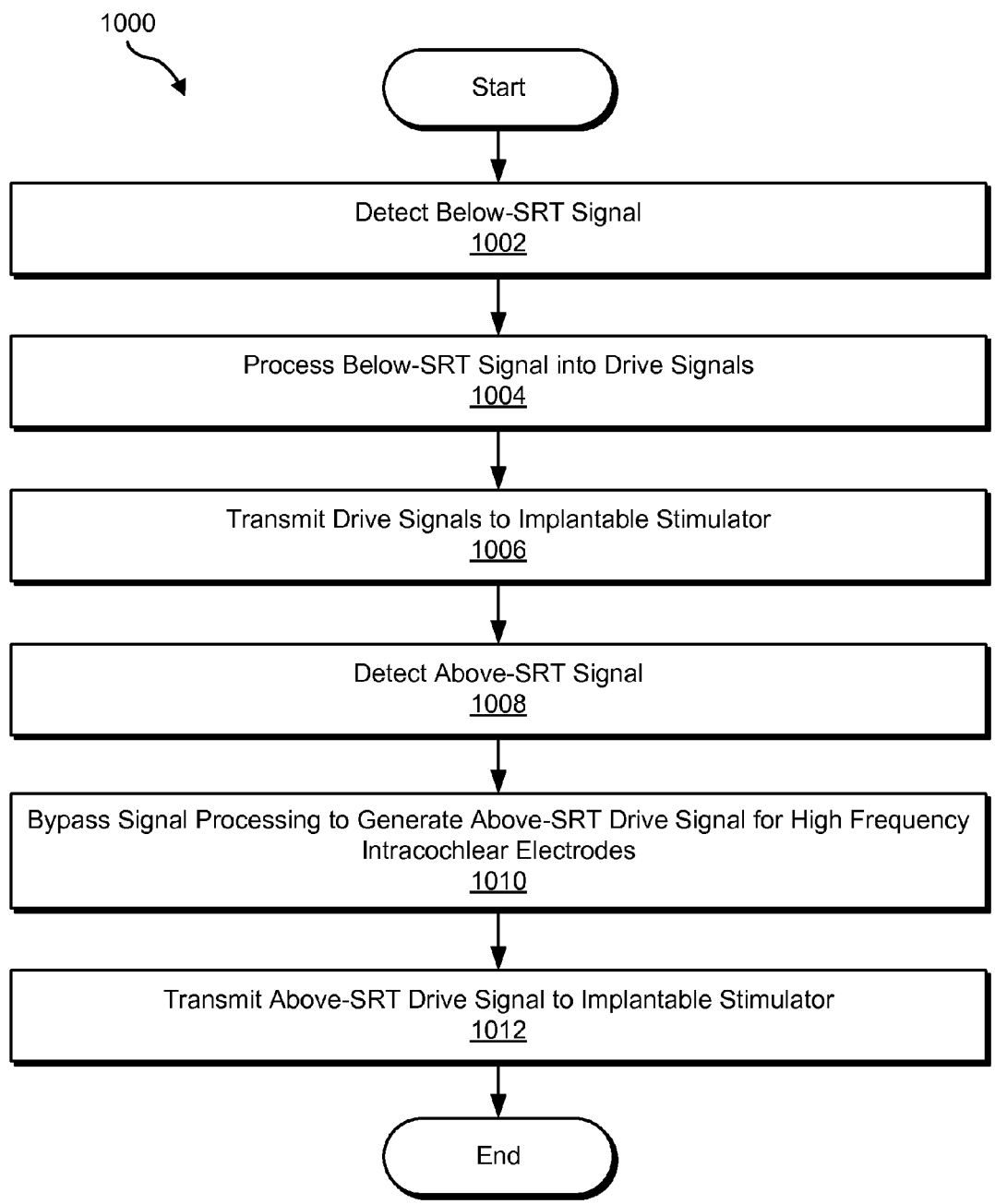
FIG. 10 illustrates an exemplary method of protecting hearing using a cochlear implant system according to principles described herein.

FIG. 10 illustrates another exemplary method 1000 of eliciting the stapedial reflex of a user using a stapedial electrode. While FIG. 10 illustrates exemplary steps according to one embodiment, other exemplary implementations may omit, add to, reorder, and/or modify any of the steps shown in FIG. 10. One or more of the steps shown in FIG. 10 may be performed by a sound processor 104 and/or any implementation thereof.

The method 1000 may include detecting, at step 1002, a below-SRT signal, processing, at step 1004, the below-SRT signal into drive signals, and transmitting, at step 1006, the drive signals to the implantable stimulator 106 in the same manner as for the method 900 using the sound processor 104.

At step 1008, the sound processor 1004 the sound processor 104 detects an above-SRT signal in the same manner as for the method 900.

At step 1010, the sound processor 104 responds to the above-SRT signal by bypassing signal processing to generate a drive signal for high frequency electrodes 206 of the intracochlear electrodes 206 positioned in the cochlea of the user. As noted above, in many users with hearing loss, low-frequency hearing may still be present whereas high-frequency hearing is significantly impaired. According, a drive signal generated by the sound processor 104 in response to the above-SRT signal may direct the implantable stimulator 106 to only stimulate those electrodes 206 corresponding to higher frequencies (e.g., above 1000 Hz) and refraining from stimulating those electrodes 206 corresponding to lower frequencies (e.g., below 1000 Hz). The drive signal generated in response to the above-SRT signal may direct the implantable stimulator 106 to stimulate the high frequency electrodes 206 at a level sufficiently high to elicit the user's stapedial reflex, i.e., trigger the user's nervous system to contract the stapedius muscle.

The drive signal generated in response to the above-SRT signal may not be based on actual frequency content and/or amplitude of the above-SRT signal, i.e., the stimulation current generated by the implantable stimulator 106 in response to the drive signal will not be configured to cause the user to perceive a representation of the actual above-SRT signal, but rather perceive a sound configured to elicit the stapedius reflex of the user. In some embodiments, the drive signal in response to the above-SRT signal may be configured to instruct the implantable stimulator to apply stimulation current to the high-frequency electrodes 206 at a most comfortable level ("M level") associated with the user, which may be at SRT level. High-frequency electrodes 206 may be at least a portion of those electrodes corresponding to frequencies above 1 kHz. In particular, the stimulation current in response to the drive signal may be such that it does not result in damage to the hearing or other tissues of the user. Bypassing signal processing to generate the drive signal in response to the above-SRT signal at step 1010 may include using a software or hardware bypass in the same manner as for the method 900.

At step 1012, the sound processor 104 transmits the drive signal from step 1010 to the implantable electrode 106, which then generates corresponding stimulation current that is applied to the electrodes 206, specifically the high-frequency electrodes 206. The stimulation current applied to the high-frequency electrodes may be effective to elicit the stapedius reflex of the user effective to attenuate vibrations reaching the cochlea of the user by at least 25 dB.

Figure 11:
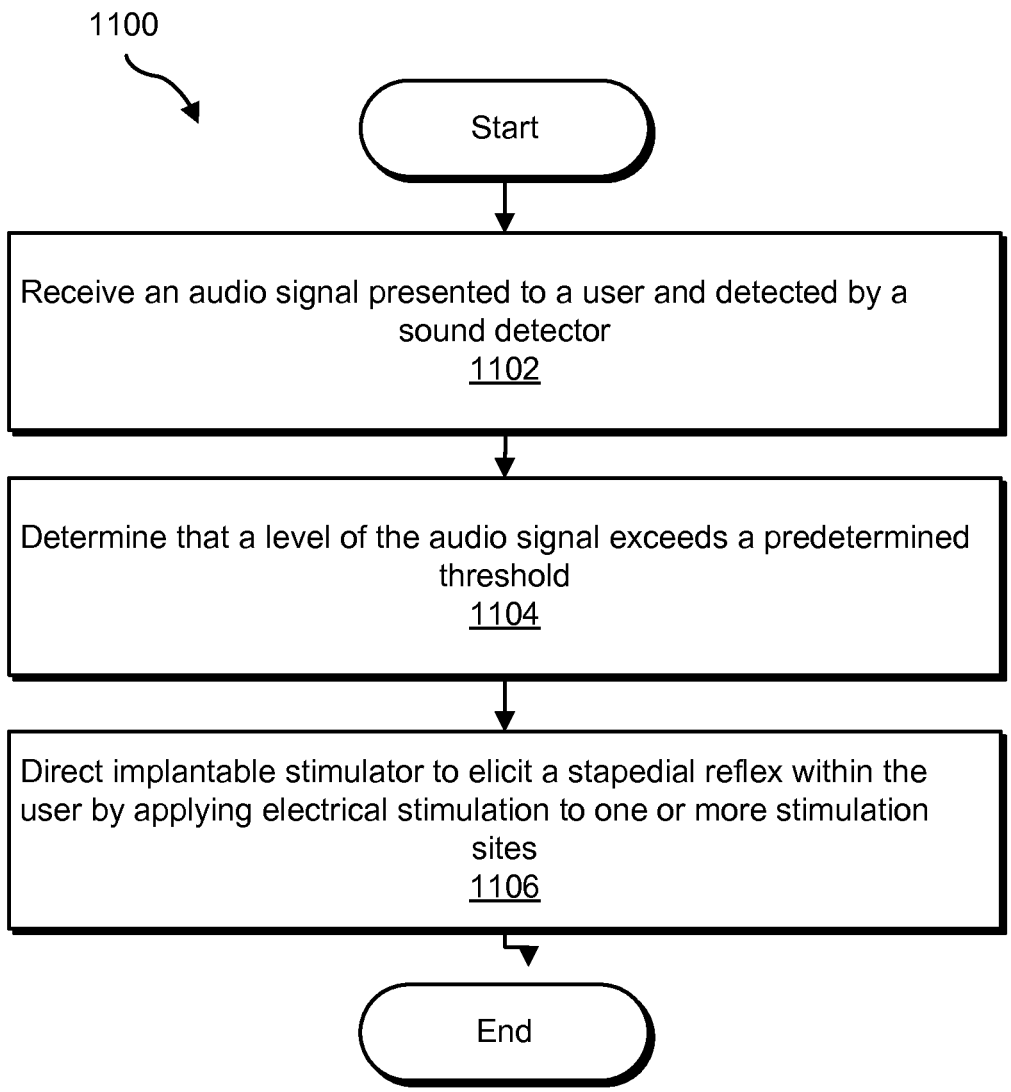
FIG. 11 illustrates a method of protecting hearing by stimulating one or more stimulation sites within a user.

FIG. 11 illustrates an exemplary method 1100 of eliciting the stapedial reflect of a user. While FIG. 11 illustrates exemplary steps according to one exemplary implementation, other implementations may omit, add to, reorder, and/or modify any of the steps shown in FIG. 11. One or more of the steps shown in FIG. 11 may be performed by sound processor 104 and/or any implementation thereof.

In step 1102, a sound processor receives an audio signal presented to the user and detected by a sound detector. For example, a sound detector 102 may detect the audio signal and produce an output received by the sound processor 104.

In step 1104, the sound processor determines whether a level of the audio signal exceeds a predetermined threshold, such as a threshold corresponding to an estimate of the SRT of the user. Step 1104 may be performed in any of the ways described herein.

In step 1106, the sound processor directs the implantable stimulator to elicit the stapedial reflex within the user by applying electrical stimulation to one or more stimulation sites. For example, electrical stimulation may be directed to be applied to a stapedial electrode 108 or to high frequency electrodes 206 of an intracochlear electrode array as described hereinabove.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a sound detector configured to detect an audio signal;
   an implantable stimulator configured to be implanted within a user; and
   a sound processor communicatively coupled to the implantable stimulator and the sound detector, the sound processor configured to
      determine that a volume level of the audio signal exceeds a predetermined threshold volume level as a result of a loud noise included within the audio signal as detected by the sound detector, and
      direct, in response to the determination that the volume level of the audio signal exceeds the predetermined threshold volume level as a result of the loud noise, the implantable stimulator to elicit a stapedial reflex within the user by applying electrical stimulation to one or more stimulation sites within the user.

2. The system of claim 1, further comprising:
   a stapedial electrode communicatively coupled to the implantable stimulator and configured to be coupled to at least one of a stapedius tendon and a stapedius muscle of the user;
   wherein the sound processor is configured to direct the implantable stimulator to elicit the stapedial reflex by applying the electrical stimulation to at least one of the stapedius tendon and the stapedius muscle by way of the stapedial electrode.

3. The system of claim 1, further comprising:
an intracochlear electrode array communicatively coupled to the implantable stimulator and configured to be implanted within a cochlea of the user;
wherein the sound processor is configured to direct the implantable stimulator to elicit the stapedial reflex by applying the electrical stimulation to one or more locations within the cochlea by way of the intracochlear electrode array.

4. The system of claim 3, wherein the electrical stimulation has a current level substantially equal to a most comfortable level ("M level") associated with the user.

5. The system of claim 1, further comprising:
an intracochlear electrode array communicatively coupled to the implantable stimulator and configured to be implanted within a cochlea of the user;
wherein the sound processor is further configured to direct the implantable stimulator to apply electrical stimulation representative of the audio signal by way of the intracochlear electrode array.

6. The system of claim 1, further comprising:
an intracochlear electrode array communicatively coupled to the implantable stimulator and configured to be implanted within a cochlea of the user;
wherein the sound processor is further configured to abstain, in response to the determination that the volume level of the audio signal exceeds the predetermined threshold volume level as a result of the loud noise, from directing the implantable stimulator to apply electrical stimulation representative of the audio signal by way of the intracochlear electrode array.

7. The system of claim 6, wherein:
the sound detector is further configured to detect an additional audio signal; and
the sound processor is further configured to
determine that a volume level of the additional audio signal does not exceed the predetermined threshold volume level, and
direct, in response to the determination that the volume level of the additional audio signal does not exceed the predetermined threshold volume level, the implantable stimulator to apply electrical stimulation representative of the additional audio signal by way of the intracochlear electrode array.

8. The system of claim 6, wherein the sound processor is configured to abstain from directing the implantable stimulator to apply the electrical stimulation representative of the audio signal by way of the intracochlear electrode array by bypassing sound processing logic, the sound processing logic configured to generate drive signals configured to direct the implantable stimulator to apply electrical stimulation representative of the audio signal by way of the intracochlear electrode array.

9. The system of claim 1, wherein the sound processor determines that the volume level of the audio signal exceeds the predetermined threshold volume level as a result of the loud noise by detecting that the volume level of the audio signal is going to exceed the predetermined threshold volume level as a result of the loud noise before the audio signal actually exceeds the predetermined threshold volume level as a result of the loud noise.

10. The system of claim 1, wherein the application of the electrical stimulation to the one or more stimulation sites is configured protect hearing in the user by forcing a stapedius muscle within the user to be in a contracted state while the audio signal is processed by the user.

11. The system of claim 1, wherein the one or more stimulation sites include a stapedius muscle of the user.

12. The system of claim 1, wherein the one or more stimulation sites include a high-frequency portion of a cochlea of the user.

13. The system of claim 1, wherein the electrical stimulation is configured to attenuate vibrations reaching a cochlea of the user by at least 25 dB.

14. A method comprising:
receiving, by a sound processor, an audio signal presented to a user and detected by a sound detector;
determining, by the sound processor, that a volume level of the audio signal exceeds a predetermined threshold volume level as a result of a loud noise included within the audio signal as detected by the sound detector; and
directing, by the sound processor in response to the determination that the volume level of the audio signal exceeds the predetermined threshold volume level as a result of the loud noise, an implantable stimulator to elicit a stapedial reflex within the user by applying electrical stimulation to one or more stimulation sites within the user.

15. The method of claim 14, wherein the one or more stimulation sites include a stapedius muscle of the user.

16. The method of claim 14, wherein the one or more stimulation sites include a high-frequency portion of a cochlea of the user.

17. The method of claim 14, wherein the electrical stimulation is configured to attenuate vibrations reaching a cochlea of the user by at least 25 dB.

18. A system comprising:
a sound detector configured to detect an audio signal;
an implantable stimulator configured to be implanted within a user; and
a sound processor communicatively coupled to the implantable stimulator and the sound detector, the sound processor configured to
determine that a volume level of the audio signal exceeds a predetermined threshold volume level as a result of a loud noise included within the audio signal as detected by the sound detector, the determination performed by detecting that the volume level of the audio signal is going to exceed the predetermined threshold volume level as a result of the loud noise before the audio signal actually exceeds the predetermined threshold volume level as a result of the loud noise, and
direct, in response to the determination that the volume level of the audio signal exceeds the predetermined threshold volume level as a result of the loud noise, the implantable stimulator to elicit a stapedial reflex within the user by applying electrical stimulation to one or more stimulation sites within the user to protect hearing in the user by forcing a stapedius muscle within the user to be in a contracted state while the audio signal is processed by the user.

19. The system of claim 18, further comprising:
an intracochlear electrode array communicatively coupled to the implantable stimulator and configured to be implanted within a cochlea of the user;
wherein the sound processor is further configured to abstain, in response to the determination that the volume level of the audio signal exceeds the predetermined threshold volume level as a result of the loud noise, from directing the implantable stimulator to apply electrical stimulation representative of the audio signal by way of the intracochlear electrode array.

20. The system of claim 18, wherein:

the sound detector is further configured to detect an additional audio signal; and the sound processor is further configured to determine that a volume level of the additional audio signal does not exceed the predetermined threshold volume level, and direct, in response to the determination that the volume level of the additional audio signal does not exceed the predetermined threshold volume level, the implantable stimulator to apply electrical stimulation representative of the additional audio signal by way of the intracochlear electrode array.

* * * * *